United States Patent
Sneujink (10) Patent No.: US 9,372,140 B2
(45) Date of Patent: Jun. 21, 2016

(54) METHOD AND DEVICE FOR DETERMINING SHEARING STRESS OR VISCOSITY

(71) Applicant: Laurentius Gerhardus Maria Sneujink, Sint Philipsland (NL)

(72) Inventor: Laurentius Gerhardus Maria Sneujink, Sint Philipsland (NL)

(73) Assignee: INGENIEURS BUREAU ESQUISSE B.V., Sint Philipsland (NL)

( * ) Notice: Subject to any disclaimer, the term of this patent is extended or adjusted under 35 U.S.C. 154(b) by 295 days.

(21) Appl. No.: 13/974,238

(22) Filed: Aug. 23, 2013

(65) Prior Publication Data

US 2014/0053638 A1 Feb. 27, 2014

Related U.S. Application Data (63) Continuation of application No. PCT/NL2011/050117, filed on Feb. 27, 2012.

(51) Int. Cl.
G01N 11/14 (2006.01)
G01N 11/10 (2006.01)
G01N 11/16 (2006.01)

(52) U.S. Cl.
CPC ............... *G01N 11/14* (2013.01); *G01N 11/10* (2013.01); *G01N 11/16* (2013.01)

(58) Field of Classification Search
CPC ........ G01N 11/16; G01N 11/10; G01N 11/14
See application file for complete search history.

(56) References Cited

U.S. PATENT DOCUMENTS

| | | | | |
|---|---|---|---|---|
| 3,712,117 A * | 1/1973 | Fitzgerald | ............ | G01N 11/162 137/92 |
| 4,148,216 A * | 4/1979 | Do | .................... | G01N 33/4905 73/54.26 |
| 4,729,237 A | 3/1988 | Suzuki | | |
| 4,909,068 A * | 3/1990 | Miura | .................. | G01N 11/162 73/32 A |
| 5,596,139 A * | 1/1997 | Miura | .................. | G01F 23/2967 73/54.24 |
| 5,621,165 A * | 4/1997 | Miura | .................... | G01N 11/16 73/54.24 |
| 5,723,771 A * | 3/1998 | Miura | .................. | G01N 11/162 73/54.24 |
| 7,444,245 B2 * | 10/2008 | Pfeiffer | ............... | G01F 23/2965 702/137 |
| 7,530,268 B2 * | 5/2009 | Lopatin | ............... | G01F 23/2967 340/621 |
| 2013/0167620 A1 * | 7/2013 | Haeusler | ................ | G01N 11/16 73/54.41 |

FOREIGN PATENT DOCUMENTS

| | | |
|---|---|---|
| DE | 487207 C | 12/1929 |
| DE | 19510351 C1 | 8/1996 |
| EP | 0317356 A2 | 5/1989 |

OTHER PUBLICATIONS

PCT Application No. PCT/NL2012/050117—published as WO 2012/11520.

* cited by examiner

*Primary Examiner* — Daniel S Larkin
*Assistant Examiner* — Jamar Ray
(74) *Attorney, Agent, or Firm* — Banner & Witcoff, Ltd.

(57) ABSTRACT

The present invention comprises a device for measuring at least one property of a substance or medium such as the viscosity, the shearing stress, the specific weight and whether the substance or the medium shows Newtonian behavior. The device comprises a carrier arranged at least at one attachment point, a pivot arm connected pivotally or rotatably to the carrier at a rotation point located at a distance from the attachment point, a drive acting selectively on the pivot arm for driving the pivot arm in an oscillating movement, and a measurement setup for measuring the oscillation of the pivot arm to be caused with a drive, characterized in that a center of inertia lies substantially at the attachment point.

14 Claims, 8 Drawing Sheets

METHOD AND DEVICE FOR DETERMINING SHEARING STRESS OR VISCOSITY

CROSS-REFERENCE TO RELATED APPLICATIONS

This application is a continuation of pre-AIA PCT Application No. PCT/NL2012/050117 filed Feb. 27, 2012, and published in the English language as PCT Publication No. WO 2012/115520 on Aug. 30, 2012. The PCT Application claims priority from Netherlands Appln. No. 2006304, filed Feb. 25, 2011. These documents are hereby incorporated herein by reference.

FIELD OF THE INVENTION

The present invention relates to a device for measuring at least one property of a substance or medium such as the viscosity, the shearing stress, the specific weight and whether the substance or the medium shows Newtonian behavior. Such a device is generally known.

BACKGROUND OF THE INVENTION

Important properties of a substance or medium are the viscosity, the shearing stress, the specific weight and whether the substance shows Newtonian behavior. These properties are measured by means of sensors or devices. This device moves a mass or object in or on the medium in order to measure these properties on the basis of the movement actually followed as a response to an excitation. This movement can be followed in all directions, i.e. in six freedoms of movement or combinations thereof. Most sensors operate with a pivot arm which forms an oscillating object and is in contact with the medium. In the known device the measurement results and conclusions to be derived therefrom about the properties of the medium are however not very reliable.

In addition, each oscillator has a resilient portion. This resilient portion is always susceptible to temperature fluctuations. The material of the spring expands or contracts under the influence of changing temperature. The dimensions of the spring hereby change and the frequency thereof will change. The Young modulus of the material, and thereby the spring constant, will also change due to change in temperature.

The pivot arm which is in contact with the medium will also change in physical size at different temperatures, whereby measurements, which correspond to and are dependent on the contact surface with the medium, are therefore also temperature-dependent.

The measurement of a shearing stress of a medium can take place by measuring the friction which the medium causes when in contact with the pivot arm in the form of an oscillating portion.

Many methods are possible for this purpose, for instance determining the damping. This is possible by measuring an amount of energy necessary to keep the oscillating system in oscillation when the oscillating system is driven near its resonance frequency. It is of course also possible to keep the added amount of kinetic energy constant and to measure changes in the movement of the pivot arm.

It is also possible to provide a fixed amount of kinetic energy at the resonance frequency of the oscillating system, wherein a change in the movement of the pivot arm caused by the medium can be measured. It is of course also possible to vary the amount of added kinetic energy so that there is a constant movement. All these methods have been known since 1950 using the Bendix type viscosity meter.

When an oscillating mass in the medium displaces the medium as a result of its own movement, the measurement will always be a combined measurement of shearing stress and specific weight.

In order to measure the specific weight of the medium a displacement of the medium must take place, which can be caused with the pivot arm as oscillating portion in the medium. This measurement can take place in the same way as determining of the shearing stress. When the pivot arm also displaces medium due to its movement in the medium, depending on the size or dimension of the frontal surface area in the direction of movement through the medium, a force will be created in the opposite direction.

SUMMARY OF THE INVENTION

The present invention has for its object to obviate or at least considerably reduce adverse effects on the ability to accurately measure the stated phenomena, for which purpose a device according to the present invention is distinguished by the features defined in the characterizing part of the independent claim of the appended claims. Undesirable effects of vibrations are effectively counteracted with a configuration in which the centre of inertia lies substantially at the attachment point. It is noted that this measure is far superior to a feature where the centre of gravity of the pivot arm is positioned at the rotation point, which would have been obvious. The present invention in contrast requires that the centre of inertia (a wholly different entity from the centre of gravity of the pivot arm alone) be located at a wholly different location, wherein the effects of vibrations are counteracted much more effectively in new and inventive manner.

The present invention has diverse additional and alternative embodiments as defined in the appended dependent claims. The device according to the invention can thus have the feature that the pivot arm is at least partially hollow on the side opposite the attachment point relative to the rotation point to an extent such that the centre of inertia of the device lies at the attachment point. It is moreover hereby possible to save on sometimes extremely costly material, this being for instance Super Invar, NiSpanC, Alloy 902 or any other material, which can be selected to prevent temperature influences on the spring constant and/or contraction or expansion. Additionally or alternatively, the pivot arm can be at least partially narrowed on the side opposite the attachment point relative to the rotation point to an extent such that the centre of inertia lies at the attachment point. Additionally or alternatively, the pivot arm can be weighted with additional mass on the side of the attachment point relative to the rotation point such that the centre of inertia lies at the attachment point.

Additionally or alternatively, the pivot arm can be weighted with additional mass on the side of the attachment point relative to the rotation point such that the center of inertia lies at the attachment point.

Additionally or alternatively the device according to the invention can have the feature that the drive comprises an electromechanical configuration with at least one controllable electromagnetic drive element, such as a coil, associated with the carrier, and at least one permanent magnet arranged on or at the pivot arm, and further comprising a source of current connected to the drive element. By utilizing a control current a variation in the resistance of the electromagnetic drive element, such as the coil, cannot affect the current flowing thereto and therethrough, as would be the case with a control voltage, since the current can have a fixed value or take a pre-known form varying in time. It can be favorable here for the source of current to comprise a voltage-current converter which is adapted to convert a control signal based on a voltage to a control signal based on a current. A control voltage can thus be generated in conventional manner and be converted to a control current in order to safeguard the evident advantages of a control current.

Additionally or alternatively in the case of a source of current, the source of current can generate a current with sawtooth variation in time corresponding to an oscillating swing of the pivot arm. It is hereby possible to take into account the distance the permanent magnet is removed from the electromagnetic drive element, such as the coil, in order to realize a repulsion or attraction of the mass of the pivot arm, or more particularly the permanent magnet thereon, associated therewith and with the path followed by the pivot arm.

Additionally or alternatively, the device according to the invention can have the feature that the measurement setup for measuring the oscillation of the pivot arm to be caused with the drive comprises a movement recording element, such as a coil, and a permanent magnet arranged on the pivot arm. The coil can be separate from the coil for excitation or form a unit therewith. A measuring resistor can measure the current through the coil induced by the magnet on the pivot arm. Allowance can be made here for the preferably current-control signal in order to eliminate or reduce cross talk from the measuring signal.

Additionally or alternatively, the device according to the invention can have the feature that the carrier comprises a housing. The side of the pivot arm above the rotation point can thus be held out of the medium for the purpose performing measurements on the movement thereof.

Additionally or alternatively, the device according to the invention can have the feature of a liquid shield, such as a cylinder, for preventing liquid flows against or along the pivot arm. Measurement can thus be performed in stationary medium, with evident advantages in respect of the reliability of the results to be obtained.

Additionally or alternatively, the device according to the invention can have the feature of an element arranged on the pivot arm for enlarging the frontal surface area of the pivot arm with the element during movement thereof through the medium. The element can be plate-like, and particularly (though not exclusively) a circular disc. Using the plate the ratio of displacement of the medium relative to the shearing stress can be made smaller, whereby during a lateral movement of the pivot arm a greater dependence on the correlation with the shearing stress is created, and thereby also a greater correlation to enable the shearing stress to be derived from a formula for calculating force. It can be advantageous here for the element to be thin relative to the longitudinal direction of the pivot arm, since the position of the center of inertia can then be best maintained without needing to take further measures, wherein further hollowing of the pivot arm or flattening thereof, or arranging a compensating mass in order to compensate for the plate, also fall within the possibilities according to the present invention.

Frequent reference is made in the following descriptions to measuring the properties of a medium. It must be noted here that the present invention can also be applied to measure properties of materials in a phase other than liquid; such as gaseous, plasma or solid. The present use is aimed mainly at determining liquid properties such as shearing stress, specific weight and Newtonian behavior.

The present invention will be further elucidated below with reference to the accompanying drawing, in which diverse embodiments are shown but in which the same reference numerals can be used for the same or similar components, elements and aspects, even if these relate to different embodiments. It is noted here that none of the shown and described embodiments must be deemed or interpreted as limiting the scope of protection of the present invention, since the scope of protection therefor is defined solely in the appended claims. In the drawing:

DETAILED DESCRIPTION OF THE INVENTION

Figure 1:
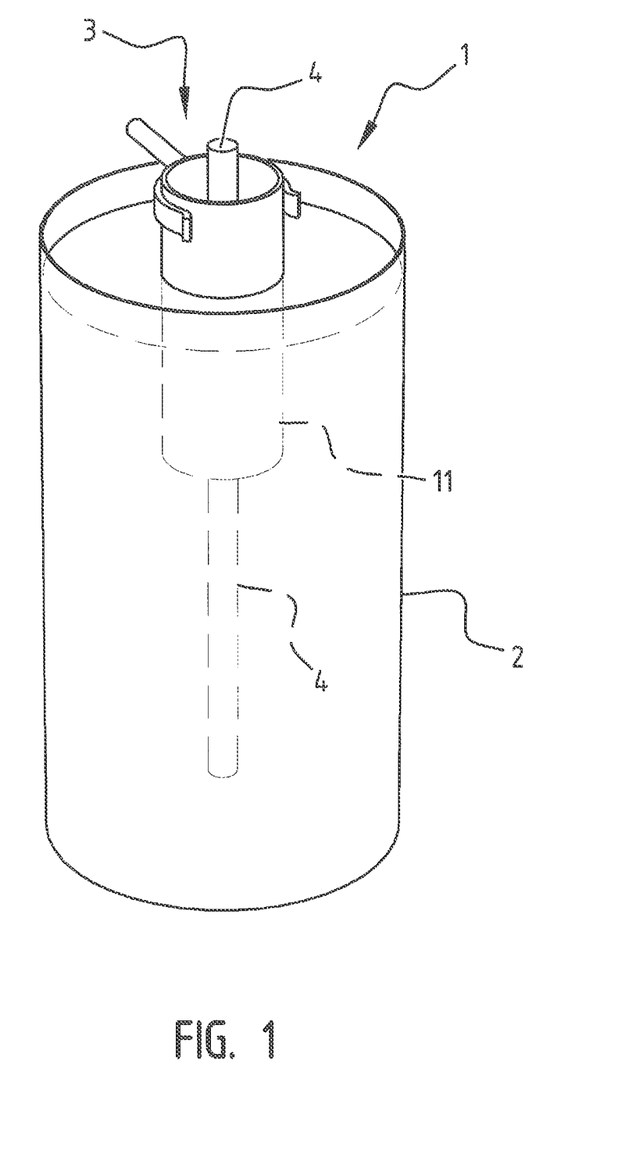
FIG. 1 is a perspective view of a device in a first embodiment of the present invention.

FIG. 1 shows a device 1 according to the present invention in a first embodiment. Device 1 comprises a cylinder 2 and a pendulum 3 with a solid pivot arm 4 in the embodiment according to FIG. 1 and a hollow pivot arm 5 in the embodiment of device 7 according to FIG. 3. Pivot arms 4, 5 are suspended tiltably from rotation point 10 in a housing 11 in order to oscillate in medium 6 in the direction of arrows A and B and back.

Figure 3:
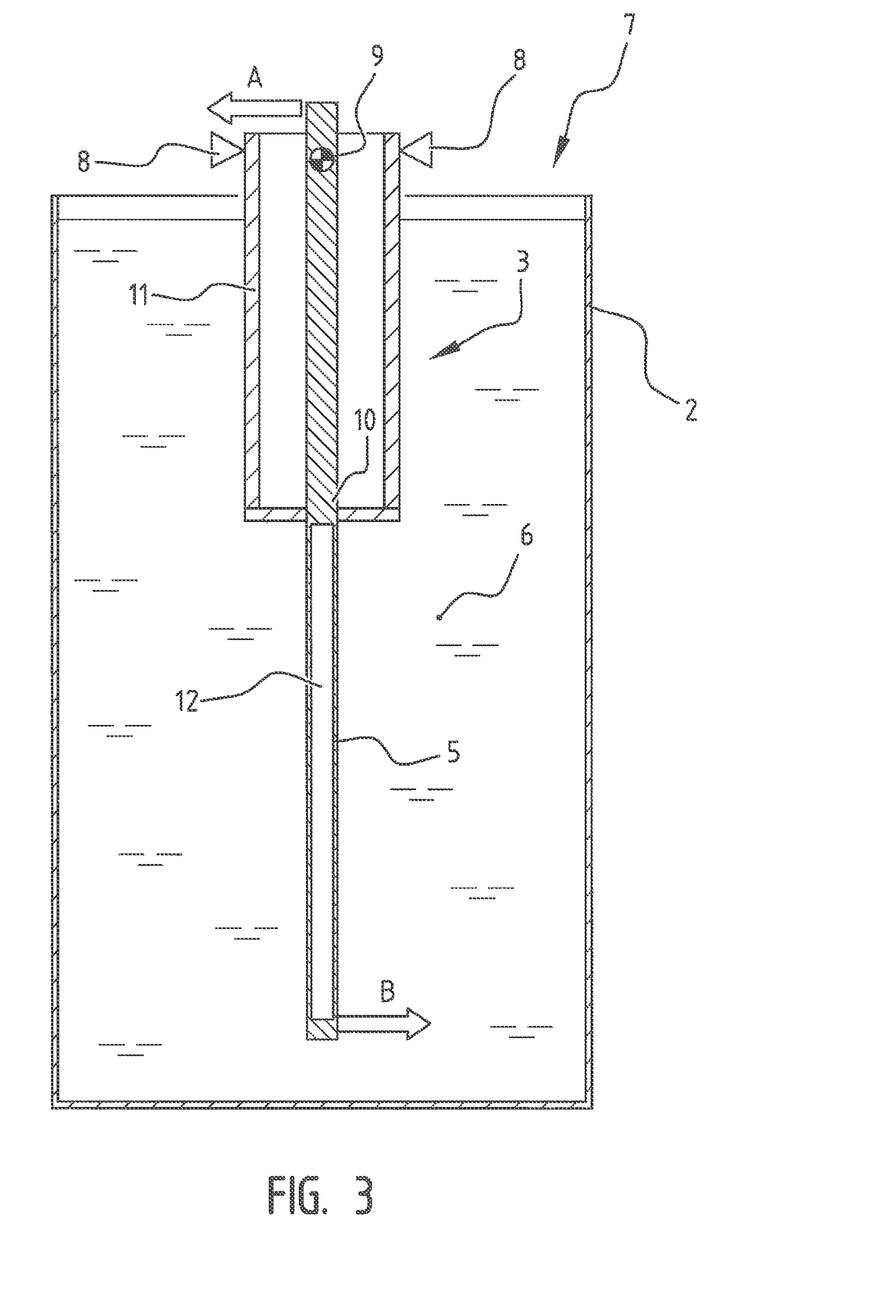
FIG. 3 shows an alternative embodiment relative to FIG. 2.

The resonating devices 1, 7 thus have a mass of pivot arms 4, 5 which move in medium 6. This mass of each of the pivot arms 4, 5 can displace the medium 6 or move about its own axis without medium being displaced. On the basis of the response of pivot arm 4 in the movement thereof through medium 6 during excitation of this movement measurement results can be generated relating to shearing stress, specific weight and whether a substance or medium 6 shows Newtonian behavior, and viscosity of the substance or medium 6.

There is found to be a measure of sensitivity to vibrations at attachment point 8 of pendulum 3. This sensitivity can be reduced or even wholly eliminated as follows. The kinetic behavior of pivot arms 4, 5 is wholly similar to that of a mass-spring system. Pivot arm 4 or 5 is here a mass and behaves as a spring. The references to spring 4, 5 and pivot arm 4, 5 are for this reason used interchangeably below.

Figure 2:
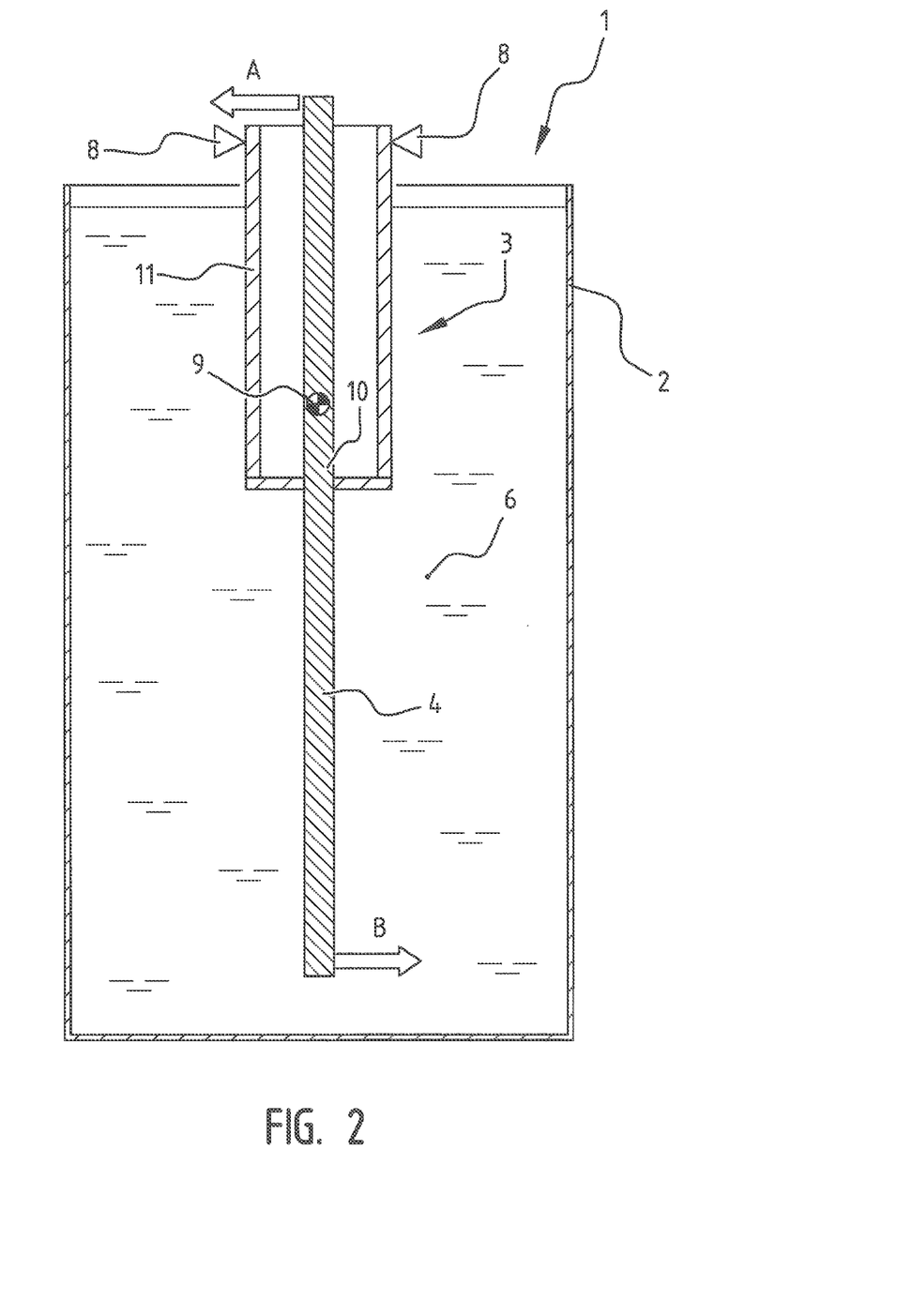
FIG. 2 is a cross-sectional side view of the device substantially as according to FIG. 1.

Spring 4, 5, or parts of spring 4, 5, can be given a hollow form in order to displace the position of the center of inertia 9 to a position which lies closer to attachment point 8 and is therefore better than if the spring is embodied in other form (for instance in the embodiment of FIG. 2). Said displacement is made clear when the position of the center of inertia in FIG. 2, with a center of inertia 9 lying close to the attachment point, is compared to that in FIG. 3, in which the center of inertia 9 lies at a greater distance from attachment point 8. In FIG. 3 this is achieved with a hollow part 12 of pivot arm 5, where in the configuration of FIG. 2 this could be achieved by adding additional mass to pivot arm 4 above rotation point 10 or by narrowing the pivot arm 4 below rotation point 10. It is noted that this approach is at variance with a development, which can be deemed by the skilled person as being more logical, of placing the center of inertia closer to rotation point 10, in the light of the wish to reduce vibrations.

Every single oscillating mass on earth must be able to push off against its surroundings. This causes vibrations which are transmitted to non-oscillating mass. For example: a tuning fork consists of two oscillating masses. Mass A, one tooth of the fork of the tuning fork, oscillates the other tooth of the fork, Mass B, with the same frequency and in opposite direction to the orientation of the tooth of the fork with Mass A. Because the resonance frequency of a first mass-spring system with mass A and the resonance frequency of the other mass-spring system with mass B are substantially identical, and the direction of displacement of the two masses is substantially in opposite direction, the kinetic energy will undergo little damping by a mass other than mass A and mass B. After a tuning fork has been set into resonance, masses A and B will hereby displace for a long time around a center.

In the case of a single oscillating mass-spring system it will be desired to reduce as far as possible the influence of masses other than the mass associated with device 1, 7.

This is possible by keeping the direction of transfer from the single oscillating mass-spring system in the same direction as the position in which the whole system is mounted, therefore in the case of devices 1 and 7 the attachment points 8. The mass present at the location where the measuring system is mounted can be predetermined and is always the same. As a consequence the oscillation of the spring or pivot arm 4, 5 will be substantially or wholly independent of ambient factors after placing in its application. The position of this imaginary point and associated direction of movement can be calculated, and this point is referred to here as the center of inertia 9. By giving an oscillating pivot arm 5 a hollow form in FIG. 3 the center of inertia 9 can be displaced in the direction of attachment points 8 in the configuration of FIG. 3 compared to the situation in FIG. 2. Dependence of placing of pivot arm 5 is hereby prevented and/or significantly reduced compared to the configuration in FIG. 2 with a solid pivot arm 4. The addition of mass at a random point on the spring or pivot arm 4, 5 further has immediate consequences due to the center of inertia 9 thereby being shifted away from an optimal point close to attachment point 8. In FIG. 2 or FIG. 3 mass can also be added above the center of inertia 9, whereby this center of inertia 9 can be displaced still further toward attachment points 8 than is already realized in FIG. 3 as compared to FIG. 2, or in order to displace this center of inertia 9 still further upward in the configuration according to FIG. 2 other than only by means of the hollow pivot arm 5 in FIG. 3.

As a result of placing of the center of inertia 9 of the pivot arm 4, 5 serving as measuring part of device 1, 7 relative to attachment point 8 of the sensor, the transfer of resonance frequencies from pivot arm 4, 5, or the measuring part of device 1, 7, to the attachment points 8 thereof is reduced. Vibrations from attachment points 8 of device 1, 7 to pivot arm 4, 5 will hereby also be reduced. Both effects contribute toward good operation of device 1, 7 in environments with many vibrations.

Pivot arm 4, 5 can be driven by means of a displacing mass at a random point along the length of pivot arm 4, 5 or electromechanically or in another manner in order to bring about a displacement of pivot arm 4, 5 in the medium. Use can be made here of different degrees of freedom of movement of all six that are available, size or amplitude and speeds or combinations thereof, of pivot arm 4, 5 or objects connected to pivot arm 4, 5, wherein different properties of the medium to be measured can be determined.

The positioning of the center of inertia 9 of device 1, 7 serves to make device 1, 7 independent of the application or conditions. When the center of inertia 9 of the moving parts, pivot arm 4, 5 of device 1, 7, lies in the plane of attachment points 8, the positioning is optimal and ambient factors and vibrations will have no effect, or at most a very limited effect, on pivot arm 4, 5 of the device.

Figure 4:
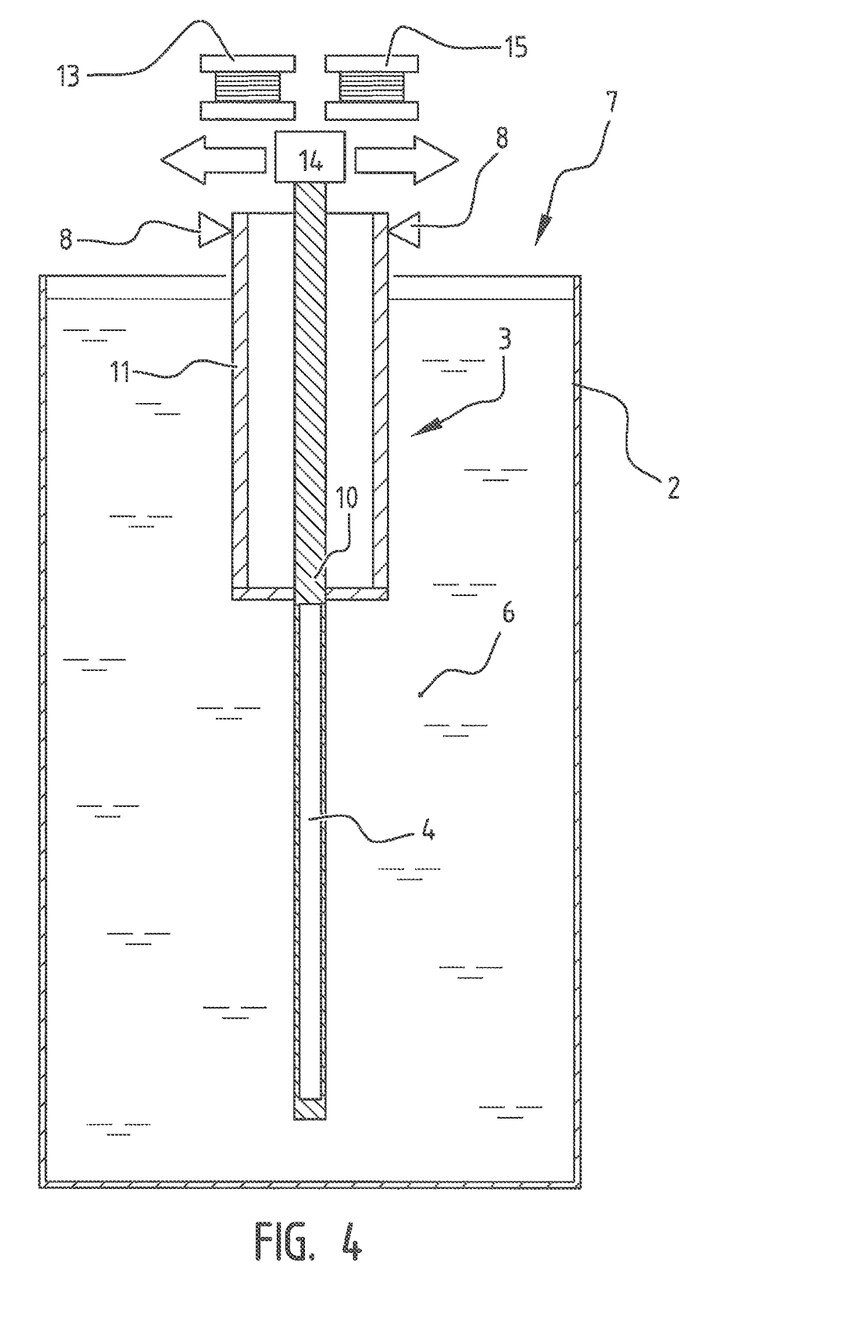
FIG. 4 shows a view corresponding to FIG. 3 with additional elements, components and aspects for generating measuring signals.

FIG. 4 shows a device 7, wherein energy for the purpose of achieving the oscillating movement is generated electromagnetically. This comprises a drive coil 13 to which an excitation signal is supplied in a manner to be described below, and a magnet 14 moving relative to coil 13. The movements are recorded electromagnetically using a receiving coil 15 in which a single is generated as a result of movement of magnet 14 along receiving coil 15.

A considerable improvement can hereby be achieved relative to previous configurations with two magnets and two electric magnetic field to electric signal converters (for instance a coil). Because both magnets move relative to both coils, there will be cross talk. In order to reduce crosstalk of signals the magnets applied had to be placed at the greatest possible mutual distance. A considerable drawback of too great a distance is that the coupling between at least one of the magnets and at least one of the coils becomes weaker. Driving and/or recording of the oscillating movement is hereby adversely affected.

By replacing the magnets in the manner shown in FIG. 4 with a single and centrally placed magnet 14, wherein drive coil 13 and receiving coil 15 can be magnetically separated from each other by means of for instance mu-metal, undesirable movements relative to the desired oscillation and incorrect recordings of the driven movements are prevented.

A single magnet 14 is thus provided which on the one hand is set into motion as a result of a current through drive coil 13 and on the other causes an alternating magnetic field in receiving coil 15 during movements, whereby movements of magnet 14 depend only on the movement followed by pivot arm 4, 5. When pivot arm 4, 5 is driven in multiple directions, or displacement is measured in multiple directions, use can be made of an alternative magnet with a plurality of equal poles, wherein the equal poles can be arranged on one side, whereby using coils placed round, at or along a path of movement an optimum coupling is created to magnet 14 on pivot arm 4, 5.

It is thus possible to keep movement of pivot arm 4, 5 better under control. Pivot arm 4, 5 which moves in medium 6, wherein displacement of medium 6 takes place, and wherein displacement of pivot arm 4, 5 is used directly or indirectly to measure shearing stress of medium 6, will encounter a counterforce due to the form of pivot arm 4, 5. This follows the formula expressed in Newton:

$$F=0.5*C*m*v^2*A$$

wherein m is the mass of the displaced medium, v is the speed of the pivot arm, A is a frontal surface area of pivot arm 4, 5 in the direction of movement and C is a constant. The constant C is determined by the form of pivot arm 4, 5 in the direction of movement. When it is wished to determine the shearing stress of medium 6, pivot arm 4, 5 will give only a derivative of the mass of displaced medium 6. On the basis of a temperature measurement of medium 6 an associated shearing stress can then be looked up when other properties of medium 6 are already pre-known.

Figure 5:
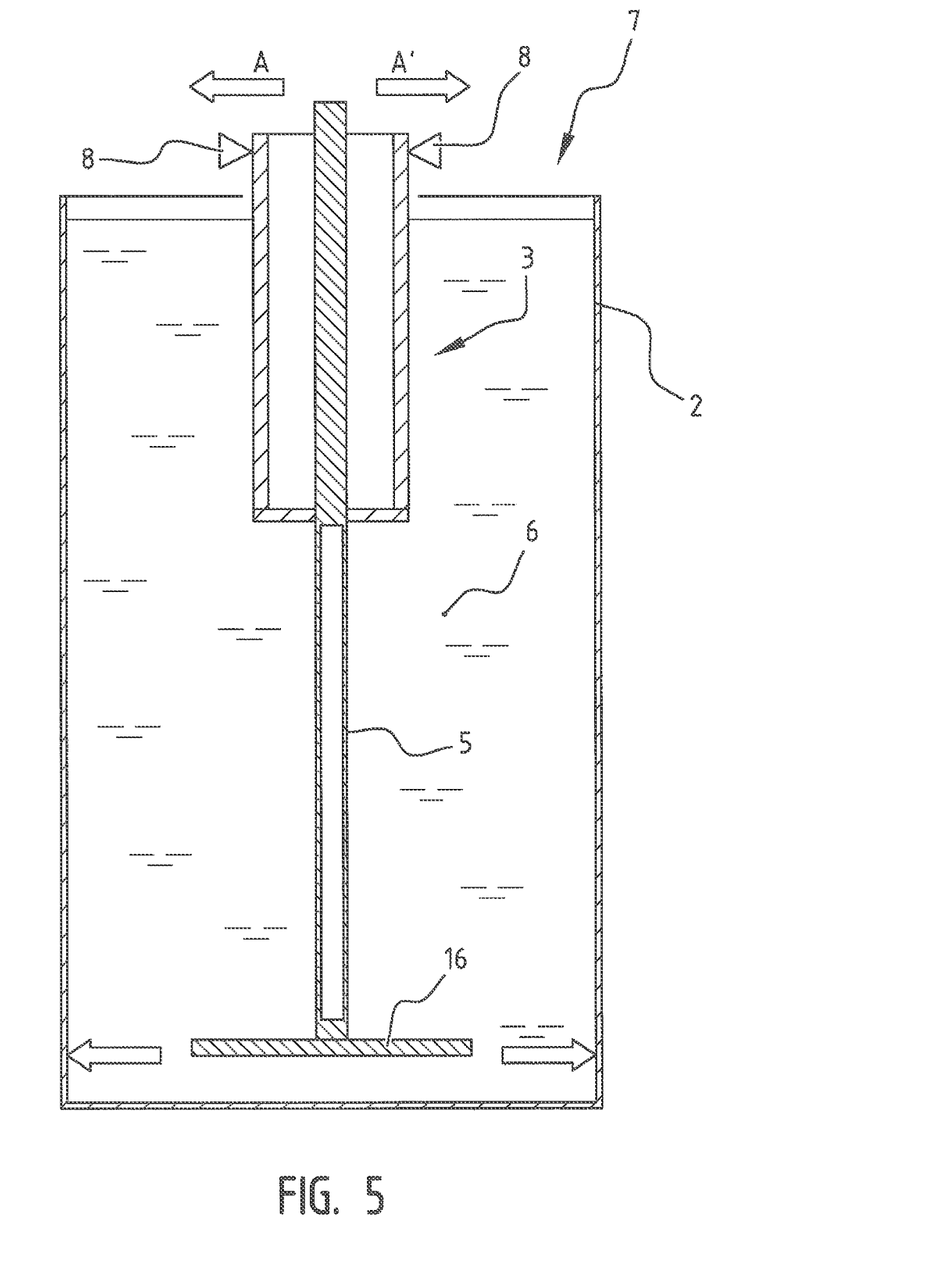
FIG. 5 and FIG. 6 show a view corresponding to FIG. 3 with an additional element.

By arranging a plate 16 on pivot arm 4, 5, wherein the surface of the plate lies substantially perpendicularly of the direction of movement of pivot arm 4, 5, the actual shearing stress of the medium can be added in the above formula. It is hereby possible to measure the shearing stress of medium 6 as direct derivative without prior knowledge of the medium 6 for measuring. The size of plate 16 determines the sensitivity in respect of the shearing stress to be measured and can be mounted removably or fixedly as desired on pivot arm 4, 5.

Plate 16 is preferably placed where the displacement of pivot arm 4, 5 is greatest in or through medium 6. Plate 16 is mounted such that the frontal surface area of pivot arm 4, 5 with plate 16 is the same in all desired directions of movement. Plate 16 is preferably round and disc-shaped.

Using plate 16 the ratio of the displacement of medium 6 relative to the shearing stress can be made smaller, whereby during a lateral movement of pivot arm 4, 5 a greater dependency on the shearing stress is created, and thereby also a greater correlation for enabling the shearing stress to be derived from the above formula.

Plate 16 is preferably relatively thin in the direction of the movement. This can also achieve that the center of inertia 9 is not displaced, or hardly so, from a desired position between or at attachment points 8.

Plate 16 can have a varying diameter, and the diameter can be chosen in accordance with prior knowledge about the medium 6 to be measured.

Figure 6:
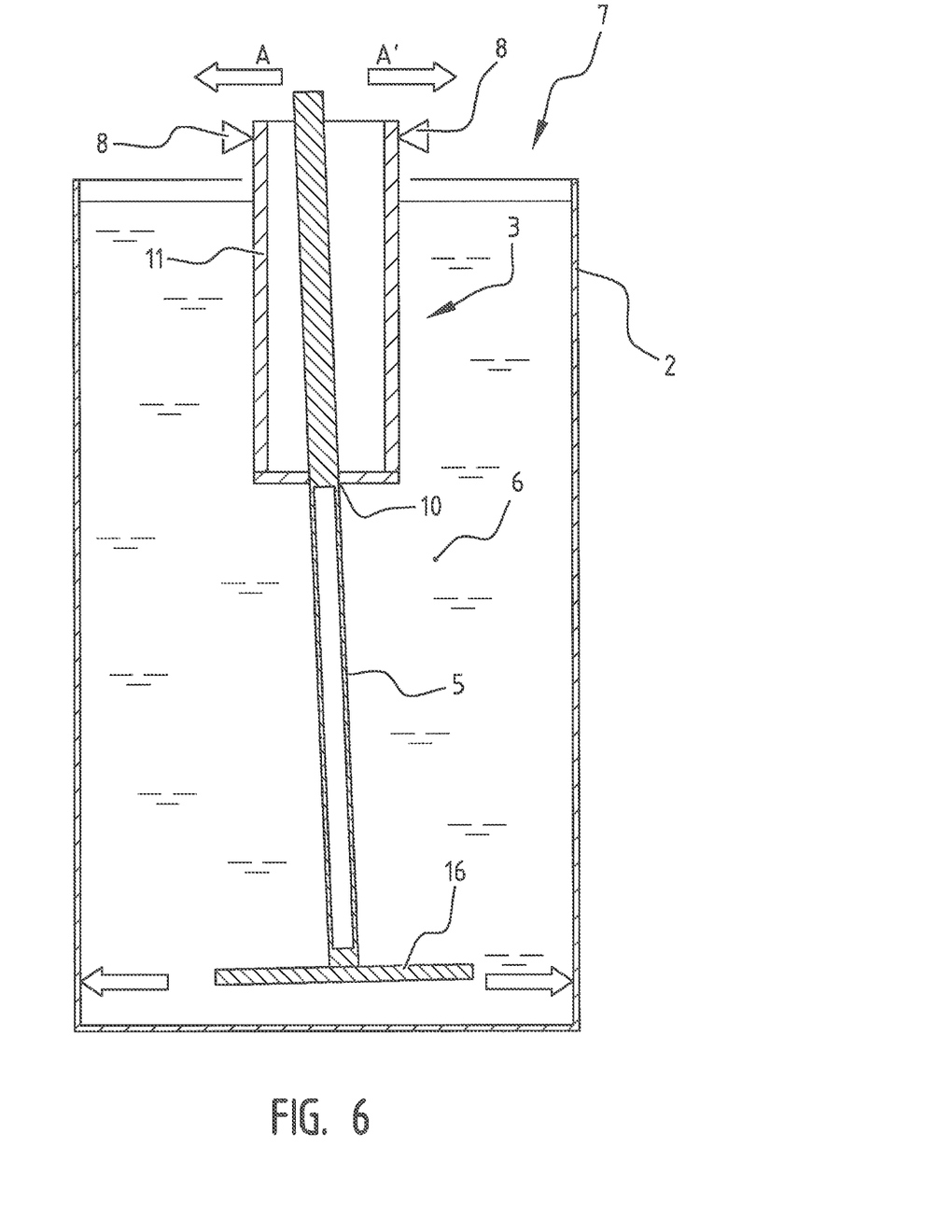

FIG. 6 shows an extreme position in the movement of pivot arm 4, 5 with plate 16 thereon. The pivot arm 4, 5 and the plate together follow a movement in the direction of arrow A and back in the direction of arrow A' for the purpose of oscillation.

Plate 16 can be mounted fixedly on pivot arm 4, 5. The amplitude of the movement is relatively small relative to the length of the part of pivot arm 4, 5 between rotation point 10 and plate 16. An inclining position of plate 16 relative to cylinder 2 or housing 11 does not affect the measurement, since pivot arm 4, 5 and plate 16 oscillate frontally through medium 6.

Figure 7:
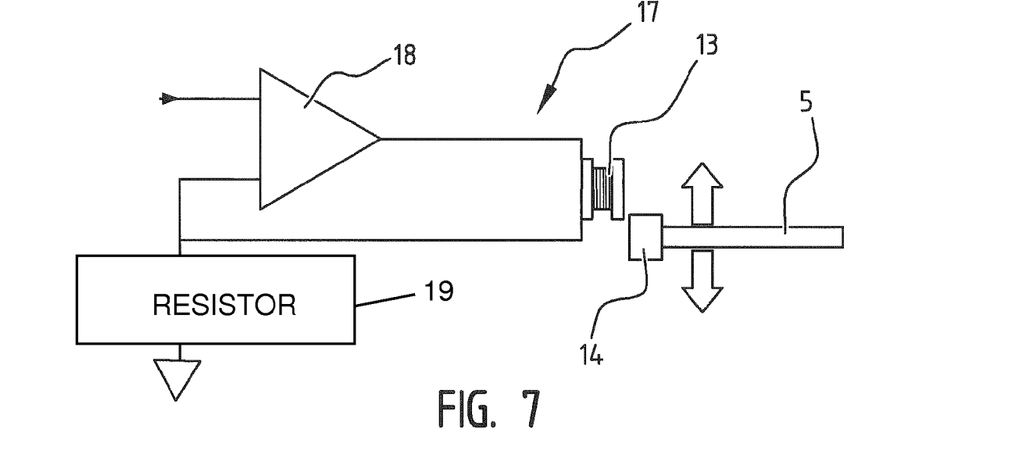
FIG. 7 and FIG. 8 show the electrical drive or excitation of or for a device according to the present invention.
Figure 8:
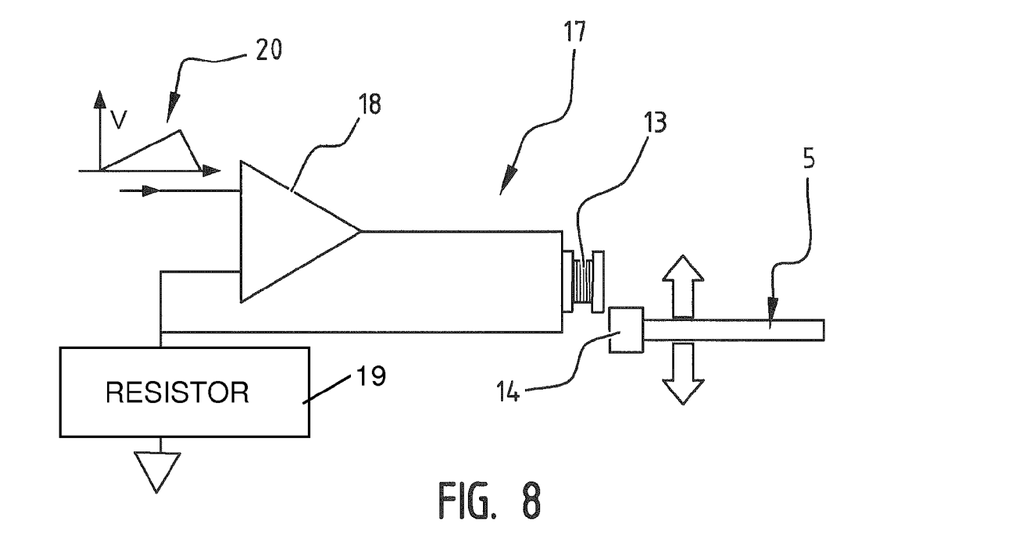

FIGS. 7 and 8 show a possible embodiment of a drive circuit 17 which can for instance be connected to drive coil 13 in FIG. 4. The drive circuit comprises a voltage-current converter in the form of an op-amp 18 and a current measuring resistor 19. The voltage-current converter in the form of op-amp 18 is supplied with a control signal based on voltage.

If the drive coil were to be driven directly on the basis of a voltage signal, as was formerly usual, the resistance of coil 13 will change as the temperature of coil 13 changes because the conductive material in the coil acquires a higher or lower resistance at the prevailing temperature relative to the previous temperature. When a resistance of or in coil 13 increases and a control voltage over coil 13 remains the same, a weaker current will flow through coil 13. This would result in a smaller amount of energy causing pivot arm 4, 5 to move in medium 6. A lower measurement value providing an indication for determining the properties of medium 6 will also result as a consequence. It is logical to compensate for this by measuring the temperature of the coil when determining the properties of the medium and to then process the measurement results accordingly before conclusions are made about the properties of the medium. It should be noted here that measuring the temperature of coil 13 can never run exactly synchronously with the moment of generation of measurement values giving the information concerning the properties of medium 6.

The embodiment according to FIGS. 7 and 8 is therefore controlled such that the current through coil 13 for a value for measurement remains constant. As a result a temperature measurement of coil 13 can be dispensed with and temperature dependence can be remedied without having to carry out compensation calculations for temperature variations, despite the fact that coil 13 is highly temperature-sensitive.

FIG. 8 shows an amplitude characteristic through time in the form of a sawtooth. This relates to a signal supplied to the input of the voltage-current converter in the form of op-amp 18. Improved control is obtained over the drive of pivot arm 4, 5 by changing this sawtooth form of the current passing through the drive coil. The current through coil 13 causes a magnetic field around coil 13. Magnet 14 on pivot arm 4, 5 begins to move in this field and, as the magnet is removed further from coil 13, the force transmitted will decrease when the current through coil 13 remains the same. This change in force applied to magnet 14 provides for a change or disruption of the movement of pivot arm 4, 5. These disruptions can be minimized by predefining the amount of current through the coil, whereby pivot arm 4, 5 makes a more uniform, and so better controllable movement. Disruptions of the movement are a disruption in the measurement.

It is noted here that influencing the movement of pivot arm 4, 5 in this way is substantially effective when the center of inertia 9 is positioned at attachment points 8. It cannot be precluded that in other configurations current control and/or a sawtooth-like amplitude characteristic can also result in a possible improvement in the oscillation behavior of a more conventional embodiment than pivot arm 4, 5.

A thus applied voltage drive of coil 13 in an electromagnetic drive for an oscillating measuring instrument or pivot arm 4, 5 formerly took the usual form of a square wave or sinusoid. The voltage characteristic of the drive of coil 13 is the derivative of the current through the coil which ensures that the current through coil 13 has a desired level at the correct moment, whereby the moment of driving of the oscillating pivot arm 4, 5 makes a controlled movement possible.

The present embodiment thus ensures that the actual current through and voltage over coil 13 is provided in a form such that the pivot arm 4, 5 moving relative to coil 13 is attracted or repulsed for the longest possible time, this providing a considerable improvement relative to a conventionally supplied square wave or sinusoid.

When the properties of a medium 6 have to be determined at different temperatures, the part of the measuring instrument which has contact with the medium undergoes expansion and contraction as a result of the temperature differences. This has particular consequences when pivot arm 4, 5 contracts or expands, since the frontal surface area of pivot arm 4, 5 which sets the medium into motion can hereby change. Expansion and contraction in this way affect the measurement. It is possible to compensate for this by means of a temperature measurement of medium 6.

Conversely, by making parts of device 1, 7 which have to come into contact with medium 6 from a metal having no coefficient of temperature expansion, the measurement signal need not be compensated for temperature. Such material is for instance the alloy Super Invar. Particularly the pivot arm 4, 5 is preferably, though not exclusively, manufactured from such a metal or such an alloy without thermal expansion coefficient. The metal or the alloy need only display no contraction or expansion within a normal range of prevailing temperatures. It is hereby possible to make the measurement signals obtained with device 1, 7 independent of prevailing temperatures.

In an embodiment of a device 1, 7, wherein the oscillating pivot arm 4, 5 is manufactured from a metal and subject to temperature fluctuations, the spring constant of the thus formed mass-spring system can change with the temperature. The drawback here is that the resonance frequency also changes. It is possible to compensate for this by measuring the temperature of the spring of the measuring instrument. The resonance frequency measurement in a medium provides much information about the physical properties of the medium.

By embodying the oscillating pivot arm 4, 5 in an alloy such as NiSpanC or Alloy 902 or another metal which can generate a temperature-independent spring constant the resonance frequency is then dependent only on the properties of medium 6. This is particularly the case for housing 11 in which pivot arm 4, 5 is arranged rotatably about rotation point 10, although parts of pivot arm 4, 5 can also be manufactured from a material such as NiSpanC or Alloy 902, particularly at positions where the pivot arm and the housing are in mechanical contact.

Figure 9:
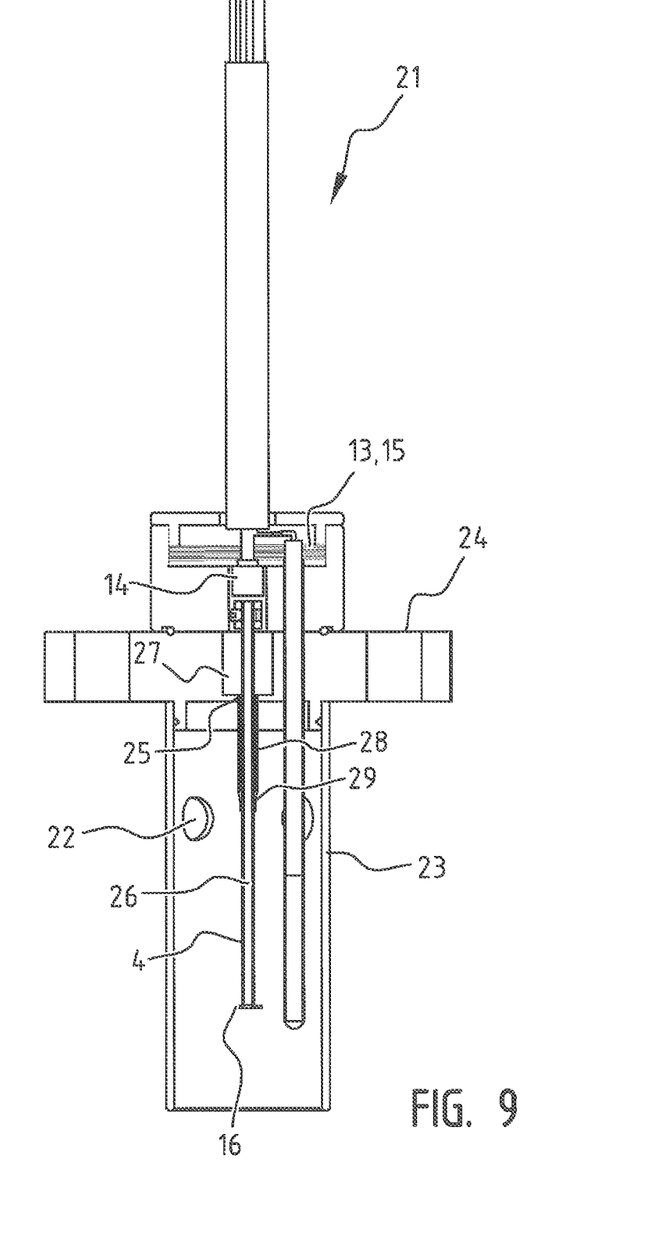
FIG. 9 shows a cross-sectional view of an embodiment of a device according to the present invention shown in more detail.

In the embodiment of FIG. 9 holes 22 are arranged in a cylinder 23 for throughflow in cylinder 23. Cylinder 23 is arranged on a flange 24 which is comparable to the attachment points 8 in the previous embodiments. Pivot arm 4, 5 with plate 16 on the freely pivotable end thereof protrudes through a passage 25 in flange 24 at a recess 27 in the flange, this passage 25 being comparable to rotation point 10. At the passage 25 where the pivot arm protrudes through flange 24 the flange 24 is thin as a result of the recess 27. Pivot arm 4, 5 can thus pivot in the passage. Pivot arm 4 is formed by a hollow tube 26 with a diameter of for instance 3 mm and for instance of Super Invar or Alloy 316. Arranged around this tube is a spring sleeve 28, preferably of the same material as tube 26, extending downward from passage 25 (rotation point 10). At a tapering end part 29, likewise preferably of the same material as tube 26 and optionally also spring sleeve 28, spring sleeve 28 is connected to tube 26. Opposite the tapering end part 29 the spring sleeve is arranged on flange 24 in passage 25. A mass-spring system capable of oscillation is formed due to the resilient properties of the materials used for tube 26, spring sleeve 28 and optionally also the tapering end part 29. Excitation takes place with a single coil 13, 15 in association with a single permanent magnet 14. Coil 13, 15 also serves to record movement of the pivot arm resulting from currents induced in coil 13, 15 by magnet 14 when the magnet moves along coil 13, 15 in the oscillating movement thereof.

After examination of the embodiments of the present invention described above and shown in the drawing many alternative and additional embodiments will become evident to the skilled person, which must then be deemed as lying outside the scope of protection only if they do not satisfy the requirements according to the appended claims.

What is claimed is:

1. A device (1, 7) for measuring at least one property of a substance or medium (6) from a group comprising: viscosity; shearing stress; specific weight; and whether the substance or the medium shows Newtonian behavior, the device comprising:
    a carrier (11) configured to be mounted to an attachment point (8) to hold the device;
    a pivot arm (4, 5) connected pivotally or rotatably to the carrier (11) at a rotation point (10);
    a drive (13, 14, 17) acting selectively on the pivot arm for driving the pivot arm (4,5) in an oscillating movement; and
    a measurement setup (15) for measuring the oscillation of the pivot arm (4,5) to be caused with the drive (13, 14, 17), wherein
    the carrier (11) extends between the attachment point (8) and the rotation point (10), whereby the rotation point (10) is located at a distance below the attachment point (8), and
    the pivot arm (4,5) is configured such that a center of inertia (9) of the device (1,7) lies at the attachment point (8).

2. The device as claimed in claim 1, wherein the pivot arm (4,5) is at least partially hollow on a side of the pivot arm (4,5) opposite the attachment point (8) relative to the rotation point (10) to an extent such that the center of inertia (9) of the device lies at the attachment point (8).

3. The device as claimed in claim 1 or 2, wherein the pivot arm (4,5) is at least partially narrowed on the side opposite the attachment point (8) relative to the rotation point (10) to an extent such that the center of inertia (9) of the device lies at the attachment point (8).

4. The device as claimed in claim 1, wherein the pivot arm (4,5) is weighted with additional mass on a side of the pivot arm (4,5), relative to the rotation point (10), that includes the attachment point (8), such that the center of inertia (9) of the device lies at the attachment point (8).

5. The device as claimed in claim 1, wherein the drive comprises an electromechanical configuration with at least one controllable electromagnetic drive element comprising a coil (13), connected to the carrier (11), and at least one permanent magnet (14) arranged on or at the pivot arm (4,5), and further comprising a source of current connected to the coil (13).

6. The device as claimed in claim 5, wherein the source of current comprises a voltage-current converter (18) which is adapted to convert a control signal based on a voltage to a control signal based on a current.

7. The device as claimed in claim 5 or 6, wherein the source of current generates a current with sawtooth variation in time corresponding to an oscillating swing of the pivot arm (4,5).

8. The device as claimed in claim 1, wherein the measurement setup (15) for measuring the oscillation of the pivot arm (4,5) to be caused with the drive (13, 14, 17) comprises a movement recording element comprising a coil (15), and a permanent magnet (14) arranged on the pivot arm.

9. The device as claimed in claim 1, wherein the carrier comprises a housing (11).

10. The device as claimed in claim 1, further comprising a liquid shield, such as a cylinder (2), for preventing liquid flows against or along the pivot arm (4,5).

11. The device as claimed in claim 1, further comprising an element (16) arranged on the pivot arm (4,5) for enlarging a frontal surface area of the pivot arm (4,5) with the element during movement thereof through the medium (6).

12. The device as claimed in claim 11, wherein the element (16) is plate-like.

13. The device as claimed in claim 11 or 12, wherein the element (16) is disc-like and round.

14. The device as claimed in claim 11 or 12, wherein the element has a thickness measured along a longitudinal direction of the pivot arm (4,5) that is less than a width measured tranverse to the longitudinal direction of the pivot arm (4,5).

\* \* \* \* \*